United States Patent [19]

Smith et al.

[11] Patent Number: 5,763,444

[45] Date of Patent: Jun. 9, 1998

[54] ANTIDEPRESSANT 1-ARYLALKYL-4-(ALKOXY PYRIDINYL)-AND 4-(ALKOXYPYRIMIDINYL) PIPERAZINE DERIVATIVES

[75] Inventors: David W. Smith, Madison; Joseph P. Yevich, Southington, both of Conn.

[73] Assignee: Bristol-Myers Squibb Company, Princeton, N.J.

[21] Appl. No.: 696,426

[22] Filed: Aug. 13, 1996

Related U.S. Application Data

[60] Provisional application No. 60/002,269 Aug. 14, 1995.

[51] Int. Cl.$^6$ ............ C07D 403/14; C07D 401/14; A61K 31/495
[52] U.S. Cl. ............ 514/253; 544/295; 544/364
[58] Field of Search ............ 514/253; 544/295, 544/364

[56] References Cited

U.S. PATENT DOCUMENTS

| | | | |
|---|---|---|---|
| 4,954,502 | 9/1990 | Smith et al. | 514/253 |
| 5,077,293 | 12/1991 | Smith et al. | 514/253 |
| 5,300,506 | 4/1994 | Smith et al. | 514/253 |

Primary Examiner—Matthew V. Grumbling

[57] ABSTRACT

Novel compound of formula I and pharmaceutically acceptable salts thereof are useful CNS agents:

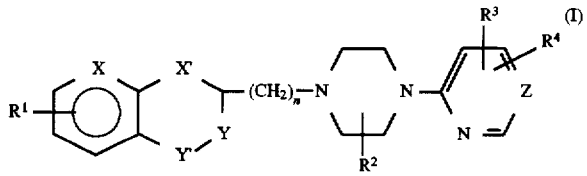

wherein
X is CH or N;
X' is CH or a direct covalent link;
Y is CH, $CH_2$ or N;
Y' is N, NH, O or S;
$R^1$ is H, Br, Cl, F, $C_{1-4}$ alkyl, $C_{1-4}$ alkoxy, $C_{1-4}$ alkoxycarbonyl, CN, $CONH_2$ or $CH_3SO_2NH$;
n is 2 or 3;
$R^2$ is H or $C_{1-4}$ alkyl;
$R^3$ is $C_{1-4}$ alkoxy;
$R^4$ is H, Br, Cl, or F; and
Z is CH or N.

14 Claims, No Drawings

ANTIDEPRESSANT 1-ARYLALKYL-4-(ALKOXY PYRIDINYL)-AND 4-(ALKOXYPYRIMIDINYL) PIPERAZINE DERIVATIVES

This application claims the benefit of U.S. Provisional Application Ser. No. 60/002,269 filed Aug. 14, 1995.

BACKGROUND OF THE INVENTION

The invention deals with heterocyclic organic compounds having bio-affecting properties, their preparation and their use. It is concerned, in particular, with di-substituted piperazines, wherein one substituent is an alkyl group bearing a benzofuran or other heterocyclic group and the second substituent is an alkoxypyridinyl or alkoxypyrimidinyl group. These compounds inhibit serotonin uptake and are, therefore, useful antidepressants.

Piperazines having alkoxypyridinyl or alkoxyprimidinyl substituents have been disclosed.

Smith et al, in U.S. Pat. No. 4,954,502, disclosed compounds of formula (i) having antidepressant properties.

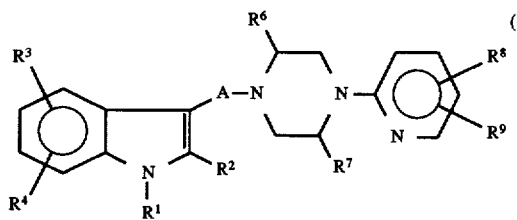

In these compounds, A is a 5 to 7 carbon cycloalkanyl or cycloalkenyl ring; $R^1$, $R^2$, $R^8$ and $R^9$ may be H or $C_{1-4}$ alkyl, $R^3$ and $R^4$ may be H, $C_{1-4}$ alkoxy, carboxamide or halogen; and $R^6$ and $R^7$ may be H or methyl.

In U.S. Pat. No. 5,077,293, Smith et al discussed antidepressant compounds of formula (ii):

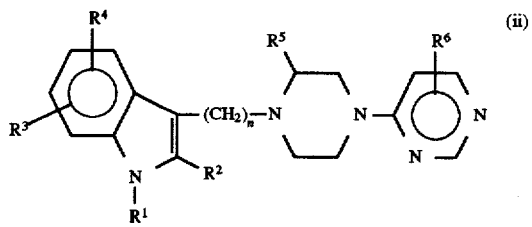

The indolyl moieties of the compounds in the patent are not the fused ring moieties found in the compounds of this invention.

Neither of these disclosures shows compounds having all of the structural features of the compounds described herein. Also, they do not teach or suggest the use of the compounds claimed herein in the treatment of depression or in pharmaceutical compositions useful for such treatment.

SUMMARY AND DETAILED DESCRIPTION OF THE INVENTION

The invention is concerned with novel piperazine compounds bearing 1-heterocyclic alkyl moieties or 4-alkoxypyridinyl or 4-alkoxypyrimidinyl moieties; use of these compounds or salts thereof as serotonin uptake inhibitors in the treatment of depression; and pharmaceutical compositions employing the compounds or their salts.

The compounds of the invention conform to formula I:

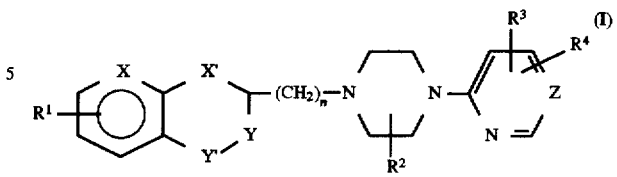

wherein
X is CH or N;
X' is CH or a direct covalent link;
Y is CH, $CH_2$ or N;
Y' is N, NH, O or S;
$R^1$ is H, Br, Cl, F, $C_{1-4}$ alkyl, $C_{1-4}$ alkoxy, $C_{1-4}$ alkoxycarbonyl, CN, $CONH_2$ or $CH_3SO_2NH$;
n is 2 or 3;
$R^2$ is H or $C_{1-4}$ alkyl;
$R^3$ is $C_{1-4}$ alkoxy;
$R^4$ is H, Br, Cl, or F; and
Z is CH or N.

X is CH or N, preferably CH.

X' is either CH or a direct covalent link. However, it is generally preferred that X' be a direct link.

Y can be a CH, $CH_2$ or N linkage. Y is generally CH or $CH_2$. Y' is chosen from N, NH, O and S. It is preferably O or S.

$R^1$ is selected from H, Br, Cl, F, $C_{1-4}$ alkyl, $C_{1-4}$ alkoxy, $C_{1-4}$ alkoxycarbonyl, CN, $CONH_2$ or $CH_3SO_2NH$. It is preferred that $R^1$ be H, Cl, or F. It is highly preferred that $R^1$ be in the 5-position of the ring. 5-methoxycarbonyl ($5-COOCH_3$); 5-amido ($5-H_2NCO$) and 5-methylsulfonamide ($5-CH_3SO_2NH$) groups are useful.

n is 2 or 3. The alkanediyl moiety at the 1-position of the piperazine ring must have no more than 3 carbon atoms and must be a straight chain.

$R^2$ may be H or $C_{1-4}$ alkyl. It is preferably H or $CH_3$. When $R^2$ is $CH_3$, it is at the 2- or 3-position on the piperazinyl group.

$R^3$ is a $C_{1-4}$ alkoxy group, preferably a methoxy group. When $R^3$ is a methoxy group, it is preferably at the 3- or 5-position on the pyridinyl or pyrimidinyl group, respectively.

$R^4$ may be H, Br, Cl, or F, but is preferably H.

Z is selected from CH or N, so that the ring is a pyridinyl moiety when Z is CH and is a pyrimidinyl moiety when Z is N.

Preferred compounds for inhibiting the neuronal reuptake of serotonin include those in the following groups:

The first preferred group of compounds include: compounds wherein R' is H or 5-Cl; X is a direct link; X' is O; Y is $CH_2$; $R^2$ is H or 2-$CH_3$; and $R^4$ is H. These compounds contain optionally substituted benzo [1,2-b,] dihydrofuran-3yl groups as well as alkoxy substituted pyridinyl or pyrimidinyl groups. Among this group is:

1-[2-(2,3-dihydro-benzo[b]furan-3-yl)ethyl)-4-(3-methoxy-2-pyridinyl)piperazine hydrochloride.

The second preferred group is made up of compounds wherein R' is H, 5-Cl, 5-F, 5-$CH_3$ or 5-$COOCH_3$; Y is —CH=; X is a direct link; X' is O; $R^2$ is H, 2-$CH_3$, or 3-$CH_3$; $R^3$ is $OCH_3$; and $R^4$ is H. Typical members of this group are compounds containing optionally substituted benzo [1,2-[b]-diydrofuran-3-yl and alkoxy substituted pyridinyl or pyrimidinyl groups. Among them are:

1-3-(5-fluorobenzo[b]furan-3-yl)propyl]-4-(3-methoxy-2-pyridinyl)piperazine hydrochloride;

1-[3-(5-chlorobenzo[b]furan-3-yl)propyl]-4-(3-methoxy-2-pyridinyl)piperazine hydrochloride;
1-[3-(5-chlorobenzo[b]furan-3-yl)propyl]-4-(5-methoxy-4-pyrimidinyl)-2-methylpiperazine hydrochloride;
1-[3-(benzo[b]furan-3-yl)propyl]-4-(5-methoxy-4-pyrimidinyl)-3-methylpiperazine hydrochloride;
1-[3-(5-methylbenzo[b]furan-3yl)propyl]-4-(5-methoxy-4-pyrimidinyl)-2-methylpiperazine hydrochloride;
1-[3-(benzo[b]furan-3-yl)propyl]-4-(3-methoxy-2-pyridinyl)piperazine hydrochloride;
1-[3-(benzo[b]furan-3-yl)propyl]-4-(5-methoxy-4-pyrimidinyl)-2-methylpiperazine hydrochloride;
1-[2-(benzo[b]furan-3-yl)ethyl]-4-(3-methoxy-2-pyridinyl)piperazine hydrochloride;
1-[2-(5-chlorobenzo[b]furan-3-yl)ethyl]-4-(3-methoxy-2-pyridinyl) piperazine hydrochloride;
1-[3-(5-fluorobenzo[b]furan-3-yl)propyl-4-(5-methoxy-4-primidinyl)piperazine hydrochloride;
1-[3-(benzo[b]furan-3-yl)propyl]-4-(5-methoxy-4-pyrimidinyl)piperazine hydrochloride;
1-[3-(5-methoxybenzo[b]furan-3-yl)propyl]-4-(5-methoxy-4-pyrimidinyl)piperazine hydochloride; and
1-[3-(5-methoxybenzo[b]furan-3-yl)propyl]-4-(3-methoxy-2-pyridinyl)piperazine hydrochloride.

The third preferred group is that group of Formula I compounds wherein $R^1$ is H; X is a direct link; X' is S; Y is $CH_2$; $R^2$ is H, 2-$CH_3$ or 3-$CH_3$; $R^3$ is $OCH_3$ and $R^4$ is H. These compounds contain benzo [-2-b] dihydrothiofuran-3-yl groups as well as alkoxy-substituted pyridinyl or pyrimidinyl groups include:

1-[2-(2,3-dihydrobenzo[b]thien-3-yl)ethyl]-4-(3-methoxy-2-pyridinyl)-2-methylpiperazine hydrochloride;
1-[2-(2,3-dihydrobenzo[b]thien-3-yl)propyl]-4-(3-methoxy-2-pyridinyl)-2-methylpiperazine hydrochloride;
1-[2-(2,3-dihydrobenzo[b]thien-3-yl)ethyl]-4-(3-methoxy-2-pyridinyl)piperazine hydrochloride;
1-[3-(2,3-dihydrobenzo[b]thien-3-yl)propyl]-4-(5-methoxy-4-pyrimidinyl)-2-methylpiperazine hydrochloride; and
1-[3-(2,3-dihydrobenzo[b]thien-3-yl)propyl]-4-(3-methoxy-2-pyridinyl)piperazine hydrochloride.

The fourth preferred group is those compounds of Formula I wherein $R^1$ is H, 5-Br, 5-CN, 5-F, 5-NHSO$_2$CH$_3$, or 5-CONH$_2$; X is a direct link; X' is S—; Y is CH; $R^2$ is H, 2-$CH_3$ or 3-$CH_3$; $R^3$ is $OCH_3$; and $R^4$ is H or 5-Cl. These molecules contain optionaly substituted benzo[1,2-b] thien-3-yl moieties along with alkoxy- or alkoxy- and chloro-substituted pyridinyl or pyrimidinyl groups. The group includes:

1-[3-(benzo[b]thien-3-yl)propyl]-4-(3-methoxy-2-pyridinyl)-2-methylpiperazine hydrochloride;
1-[3-(benzo[b]thien-3-yl)propyl]-4-(5-methoxy-4-pyrimidinyl)-3-methylpiperazine hydrochloride;
1-[3-(benzo[b]thien-3-yl)propyl]-4-(3-methoxy-2-pyridinyl)piperazine fumarate;
1-[2-(benzo[b]thien-3-yl)ethyl]-4-(3-methoxy-2-pyridinyl) piperazine hydrochloride;
1-[2-(benzo[b]thien-3-yl)ethyl]-4-(3-methoxy-2-pyridinyl)-2-methylpiperazine hydrochloride;
1-[3-benzo[b]thien-3-yl)propyl]-4-(5-methoxy-4-pyridinyl) piperazine hydrochloride;
1-[3-(benzo[b]thien-3-yl)propyl]-4-(5-chloro-3-methoxy-2-pyridinyl)-2-methylpiperazine hydrochloride;
1-[3-(5-fluorobenzo[b]thien-3-yl)propyl]-4-(5-methoxy-4-pyrimidinyl)-2-methylpiperazine hydrochloride;
1-[2-(benzo[b]thien-3-yl)ethyl]-4-(5-methoxy-4-pyrimidinyl)-3-methylpiperazine hydrochloride;
1-[3-(5-cyanobenzo[b]thien-3-yl)propyl]-4-(5-methoxy-4-pyrimidinyl)piperazine hydrochloride;
1-[3-(5-bromobenzo[b]thien-3-yl)propyl]-4-(3-methoxy-2-pyridinyl)piperazine hydrochloride;
1-[3-(benzo[b]thien-3-yl)propyl-4-(5-methoxy-4-pyrimidinyl)-2-methylpiperazine hydrochloride;
1-[3-(5-fluorobenzo[b]thien-3-yl)propyl]-4-(5-methoxy-4-pyrimidinyl)piperazine hydrochloride; and
1-[3-(5-fluorobenzo[b]thien-3-yl)propyl]-4(5-methoxy-4-pyrimidinyl)-3-methylpiperazine hydrochloride.

Of these, preferred compounds are those having IC$_{50}$ values of less than 100 nM in tests for the inhibition of synaptosomal serotonin (5-HT inhibition assay). These are listed in the following table. Compounds designated with an asterisk are most preferred, based on abilities to inhibit synoptosomal serotonin uptake.

| Example No. | Compound Name |
|---|---|
| 1 | 1-[2-(2,3-dihydro-benzo[b]furan-3-yl)ethyl]-4-(3-methoxy-2-pyridinyl)piperazine hydrochloride |
| 6* | 1-[2-(2,3-dihydro-benzo[b]thien-3-yl)ethyl]-4-(3-methoxy-2-pyridinyl)-2-methylpiperazine hydrochloride |
| 7* | 1-[2-(2,3-dihydro-benzo[b]thien-3-yl)propyl]-4-(3-methoxy-2-pyridinyl)-2-methylpiperazine hydrochloride |
| 17* | 1-[2-(2,3-dihydro-benzo[b]thien-3-yl)ethyl]-4-(3-methoxy-2-pyridinyl)piperazine hydrochloride |
| 18 | 1-[3-(2,3-dihydro-benzo[b]thien-3-yl)propyl]-4-(5-methoxy-4-pyrimidinyl)-2-methylpiperazine hydrochloride |
| 19 | 1-[3-(2,3-dihydro-benzo[b]thien-3-yl)propyl]-4-(3-methoxy-2-pyridinyl)piperazine hydrochloride |
| 20* | 1-[3-(5-fluorobenzo[b]furan-3-yl)propyl]-4-(3-methoxy-2-pyridinyl)piperazine hydrochloride |
| 25* | 1-[3-(5-chlorobenzo[b]furan-3-yl)propyl]-4-(3-methoxy-2-pyridinyl)piperazine hydrochloride |
| 27* | 1-[3-(5-chlorobenzo[b]furan-3-yl)propyl]-4-(5-methoxy-4-pyrimidinyl)-2-methylpiperazine hydrochloride |
| 28* | 1-[3-(benzo[b]furan-3-yl)propyl]-4-(5-methoxy-4-pyrimidinyl)-3-methylpiperazine hydrochloride |
| 29* | 1-[3-(5-methylbenzo[b]furan-3-yl)propyl]-4-(3-methoxy-2-pyridinyl)piperazine hydrochloride |
| 30* | 1-[3-(5-methylbenzo[b]furan-3-yl)propyl]-4-(5-methoxy-4-pyrimidinyl)-2-methylpiperazine hydrochloride |
| 31* | 1-[3-(benzo[b]furan-3-yl)propyl]-4-(3-methoxy-2-pyridinyl)piperazine hydrochloride |
| 32* | 1-[3-(benzo[b]furan-3-yl)propyl]-4-(5-methoxy-4-pyrimidinyl)-2-methylpiperazine hydrochloride |
| 33* | 1-[2-(benzo[b]furan-3-yl)ethyl]-4-(3-methoxy-2-pyridinyl)piperazine hydrochloride |
| 36 | 1-[2-(5-chlorobenzo[b]furan-3-yl)ethyl]-4-(3-methoxy-2-pyridinyl)piperazine hydrochloride |
| 37 | 1-[3-(5-fluorobenzo[b]furan-3-yl)propyl]-4-(5-methoxy-4-pyrimidinyl)piperazine hydrochloride |
| 38 | 1-[3-(benzo[b]furan-3-yl)propyl]-4-(5-methoxy-4-pyrimidinyl)piperazine hydrochloride |
| 39 | 1-[3-(5-methoxybenzo[b]furan-3-yl)propyl]-4-(5-methoxy-4-pyrimidinyl)piperazine hydrochloride |
| 40 | 1-[3-(5-methoxybenzo[b]furan-3-yl)propyl]-4-(3-methoxy-2-pyridinyl)piperazine hydrochloride |
| 41* | 1-[3-(benzo[b]thien-3-yl)propyl]-4-(3-methoxy-2-pyridinyl)-2-methylpiperazine hydrochloride |
| 50* | 1-[3-(benzo[b]thien-3-yl)propyl]-4-(5-methoxy-4-pyrimidinyl)-2-methylpiperazine hydrochloride |
| 51* | 1-[3-(benzo[b]thien-3-yl)propyl]-4-(5-methoxy-4-pyrimidinyl)-3-methylpiperazine hydrochloride |
| 52* | 1-[3-(5-fluorobenzo[b]thien-3-yl)propyl]-4-(5-methoxy-4-pyrimidinyl)piperazine hydrochloride |
| 55* | 1-[3-(5-fluorobenzo[b]thien-3-yl)propyl]-4-(5-methoxy-4-pyrimidinyl)-3-methylpiperazine hydrochloride |
| 56* | 1-[3-(benzo[b]thien-3-yl)propyl]-4-(3-methoxy-2-pyridinyl)piperazine fumarate |
| 57* | 1-[2-(benzo[b]thien-3-yl)ethyl]-4-(3-methoxy-2-pyridinyl)piperazine hydrochloride |
| 58* | 1-[2-(benzo[b]thien-3-yl)ethyl]-4-(3-methoxy-2-pyridinyl)-2-methylpiperazine hydrochloride |
| 59* | 1-[3-(benzo[b]thien-3-yl)propyl]-4-(5-methoxy-4-pyrimidinyl)piperazine hydrochloride |
| 60* | 1-[3-(benzo[b]thien-3-yl)propyl]-4-(5-chloro-3-methoxy-2- |

| Example No. | Compound Name |
| --- | --- |
| 63* | pyridinyl)-2-methylpiperazine hydrochloride<br>1-[3-(5-fluorobenzo[b]thien-3-yl)propyl]-4-(5-methoxy-4-pyrimidinyl)-2-methylpiperazine hydrochloride |
| 64* | 1-[2-(benzo[b]thien-3-yl)ethyl]-4-(5-methoxy-4-pyrimidinyl)-3-methylpiperazine hydrochloride |
| 65* | 1-[3-(5-cyanobenzo[b]thien-3-yl)propyl]-4-(5-methoxy-4-pyrimidinyl)piperazine hydrochloride |
| 71 | 1-[3-(5-bromobenzo[b]thien-3-yl)propyl]-4-(3-methoxy-2-pyridinyl)piperazine hydrochloride |

Compounds of Formula I also encompass all pharmaceutically acceptable acid addition salts (and/or solvates) thereof. The useful salts (and solvates) of the invention are those in which the counter-ion does not contribute significantly to the toxicity or pharmacological activity of the salt and, as such, they are the pharmacological equivalents of the bases of Formula I. They are generally preferred for medical usage. In some instances, they have physical properties which make them more desirable for pharmaceutical formulation, such as solubility, lack of hygroscopicity, compressibility with respect to tablet formation and compatibility with other ingredients with which the substance may be used for pharmaceutical purposes.

The salts are routinely made by admixture of a Formula I base with the selected acid preferably by contact in solution employing an excess of commonly used inert solvents such as water, ether, benzene, methanol, ethanol, ethyl acetate and acetonitrile. They may also be made by methathesis or treatment with an ion exchange resin under conditions in which the anion of one salt of the substance of the Formula I is replaced by another anion under conditions which allow for separation of the desired species, such as by precipitation from solution or extraction into a solvent, or elution from or retention on an ion exchange resin.

Pharmaceutically acceptable acids for the purposes of salt formation of the substances of Formula I include sulfuric, phosporic, hydrochloric, hydrobromic, hydroiodic, citric, acetic, benzoic, cinnamic, mandelic, phosphoric, nitric, mucic, isethionic, palmitic, heptanoic, and others.

The compounds of Formula I show potent inhibition of 5-HT reuptake and can be envisioned as potential agents for disorders associated with dysfunction in serotonergic neurotransmissions. Such disorders may include depression, anxiety, eating disorders, obesity, and drug abuse. In particular, the active compounds of the instant series are envisioned as specific agents for treating depression.

The compounds comprising the present invention inhibit the reuptake of endogenous serotonin. Selective inhibitors of serotonin uptake are effective for the treatment of mental depression and have been reported to be useful for treating chronic pain (see: R. W. Fuller, Pharmacologic Modification Serotonergic Function: Drugs for the Study and Treatment of Psychiatric and Other Disorders, "*J. Clin. Psychiatry*, 47:4 (Suppl.) April 1986, pp. 4–8). Compounds of the present invention are also envisioned to be useful in the following disorders: obsessive-compulsive disorders, feeding disorders, anxiety disorders and panic disorders.

Determination of endogenous monoaminergic re-uptake inhibition values both for serotonin and norepinephrine was accomplished using test methods described by P. Skolnick, et al., *Br. J. Pharmacology*, (1985), 86, pp. 637–644; with only minor modifications. In vitro $IC_{50}$ (nM) test values were determined for representative compounds of Formula I based on their inhibition of synaptosomal re-uptake of tritiated serotonin.

Another aspect of the instant invention provides a method for treating a mammal afflicted with depression or chronic pain which comprises administering systematically to said mammal a therapeutically effective amount of a compound of Formula I or a pharmaceutically acceptable acid addition salt thereof.

The administration and dosage regimen of compounds of Formula I is considered to be done in the same manner as for the reference compound fluoxetine, cf: Schatzberg, et al. *J. Clin. Psychopharmacology* 7/6 Suppl. (1987) pp. 4451–4495, and references therein. Although the dosage and dosage regimen must in each case be carefully adjusted, utilizing sound professional judgment and considering the age, weight and condition of the recipient, the route of administration and the nature and gravity of the illness, generally the daily dose will be from about 0.50 to about 10 mg/kg, preferably 0.1 to 2 mg.kg, when administered parenterally and from about 1 to about 50 mg.kg, preferably about 5 to 20 mg/kg, when administered orally. In some instances, a sufficient therapeutic effect can be obtained at lower doses while in others, larger doses will be required.

Systemic administration refers to oral, rectal and parenteral (i.e. intramuscular, intraveneous and subcutaneous) routes. Generally, it will be found that when a compound of the present invention is administered orally, a larger quantity of the active agent is required to produce the same effect as a similar quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, they are generally given as pharmaceutical compositions comprised of an antidepressant amount of a compound of Formula I or a phamaceutically acceptable carrier. Pharmaceutical compositions which provide from 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for parenteral compositions, such as an aqueous solution for intravenous injection or an oily suspension for intramuscular injection.

The compounds of Formula I can be prepared using processes shown in Schemes 1 through 6, below:

Scheme 1

This scheme depicts the reaction of benzofurans/benzothienes of formula 2a or dihydrobenzofurans/dihydrobenzothienes of formula 2b with 4 alkoxy-aryl piperazines of formula 3 to yield compounds of formulas 1a and 1b.

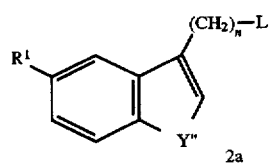
2a
or
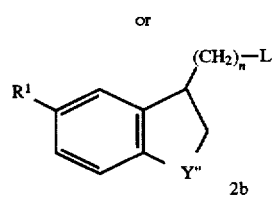
2b
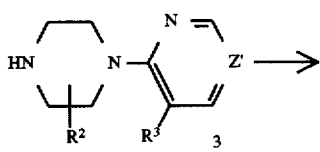
3
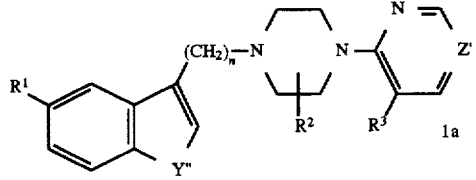
1a
or
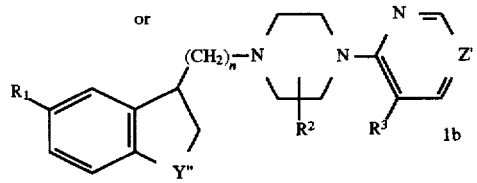
1b
$R^1$ is H, halogen, $C_{1-4}$ alkoxy, $C_{1-4}$ alkyl or nitrile;
Y" is O or S.
Z' is N or $CR^5$ ($R^5$=H or halogen);
$R^2$ and $R^3$ are defined above.
Scheme 2
Compounds of the 2,3-dihydrobenzo[b]furanyl (1b, Y"=O) and 2,3-dihydrobenzo[b]thienyl (1b Y"=S) types were prepared as shown in Scheme 2.
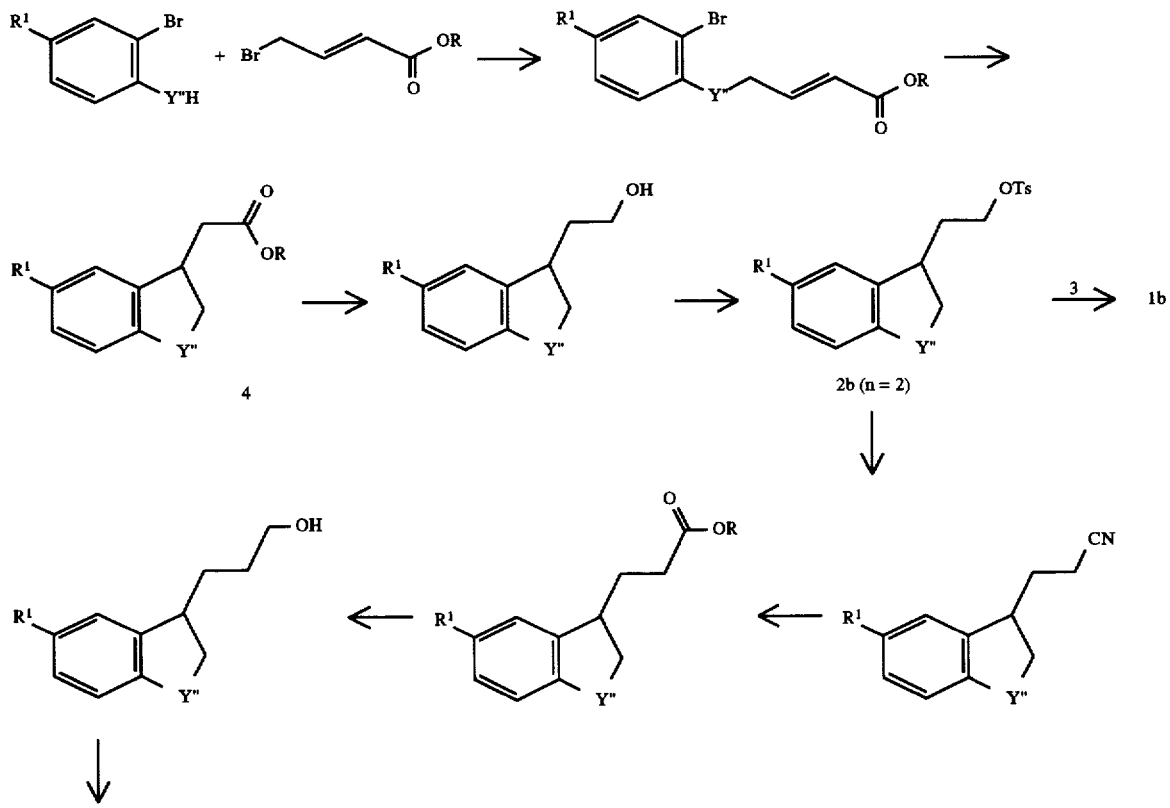

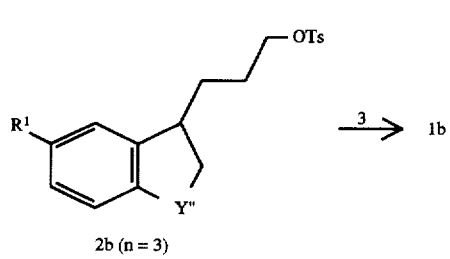
Ts is tosylate.
Compounds of the benzo[b]furanyl (1a, Y"=O) and benzo[b]thienyl (1a, Y"=S) types were prepared as shown in Schemes 3, 4 & 5.
Scheme 3.
4 ⟶
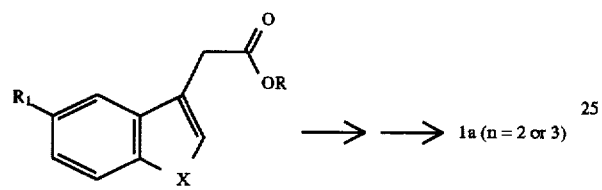
Scheme 4.
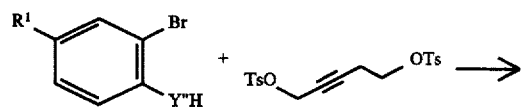
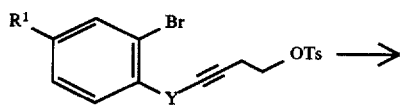
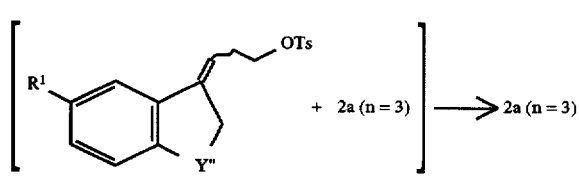
Scheme 5.
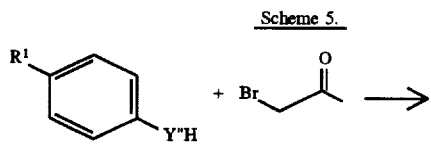
-continued
Scheme 5.
Scheme 6
This scheme is an alternative method for making the compounds of the invention. The final reduction of the amide carbonyl can be carried out using well known reagents.

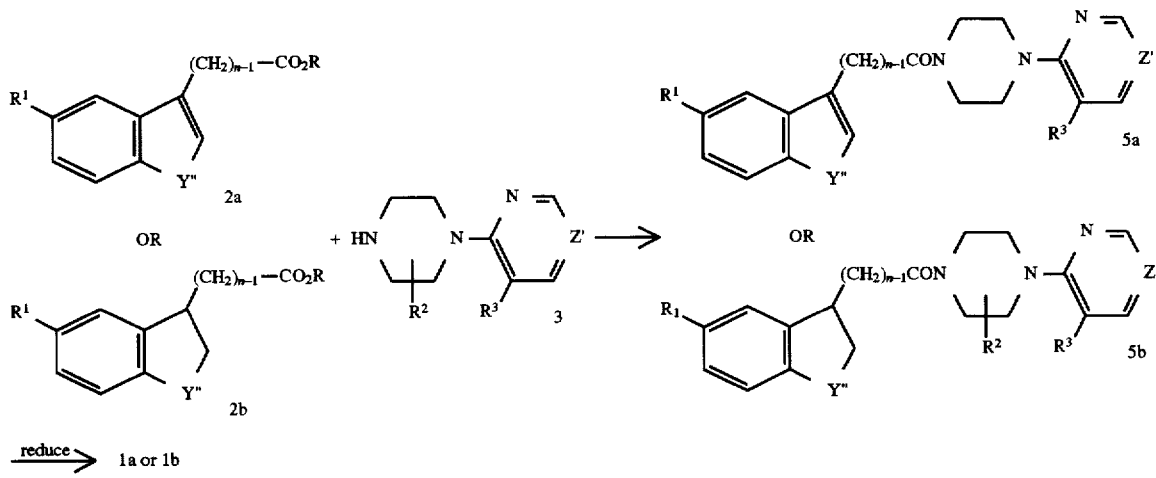

The reactions employed in Schemes 1 through 6 and their application are familiar to the practitioner skilled in organic synthesis and modifications of conditions and reagents would be readily understood. The skilled synthetic chemist would know how to adapt these processes for preparation of specific Formula I compounds, including other compounds embraced by this invention but not specifically disclosed. Variations of the methods to produce the same compounds in somewhat different fashion will also be evident to one skilled in the art. To provide greater detail in description, representative synthetic examples are provided infra in the "Specific Embodiments" section.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate synthetic processes, temperatures are expressed in degrees Celsius and melting points are uncorrected.

Analytical thin-layer chromatography (TLC) was performed on 0.25 mm EM silica gel 60 F-254 coated glass plates and preparative flash chromatography was performed on EM silica gel (36–62 µm). The solvent systems used are reported where appropriate. All reaction, extraction and chromatography solvents were reagent grade and used without further purification, except tetrahydrofuran (THF) which was distilled from sodium/benzophenone ketyl. All non-aqueous reactions were carried out in flame-dried glassware under a nitrogen atmosphere.

EXAMPLES

Examples 1–71 set forth the preparation of specific compounds of Formula I and salts thereof produced following the general schemes set out above. The preparations are grouped according to the type of molecule being produced.

Example 72 sets forth the procedure by which certain compounds of Formula I were tested to assess their ability to inhibit synoptosomal serotonin uptake.

2,3-Dihydrobenzo[b]furan type:

Example 1

Preparation of 1-[2-(2,3-dihydro-benzo[b]furan-3-yl)ethyl]-4-(3-methoxy-2-pyridinyl)piperazine hydrochloride To $CH_3CN$ (100 mL) was added 2,3-dihydro-3-benzo[b]furanethanol tosylate (1.50 g, 4.7 mmol), 1-(3-methoxy-2-pyridinyl)piperazine (0.91 g, 4.7 mmol), anhydrous $K_2CO_3$ (1.95 g, 14.1 mmol), KI (0.04 g, 0.24 mmol), and tetra-n-butylammonium hydrogen sulfate (0.08 g, 0.24 mmol). The mixture was heated at reflux under $N_2$ atmosphere for 24 h. The reaction was concentrated in vacuo, several mL of $H_2O$ added and the reaction extracted with three portions of $CH_2Cl_2$. The combined organic extracts were washed with saturated aqueous NaCl solution, dried with anhydrous $K_2CO_3$, filtered, and concentrated in vacuo. Silica gel chromatography (EtOAc) of the concentrate afforded the free base which was treated with ethanolic HCl to yield the title compound (0.85 g, 39%, mp 100°–140° C.)

Anal. calcd. for $C_{20}H_{25}N_3O_2/2HCl/2.4H_2O$: C, 52.73; H, 7.04; N, 9.23. Found: C, 53.04; H, 6.91; N, 9.10. DCI MS: $(M+H)^+$ m/e=340

Example 2

Preparation of 2 3-dihydro-3-benzo[b]furanethanol tosylate:

To $CH_2Cl_2$ (50 mL) at 0° C. was added 3-(2-hydroxyethyl)-2,3-dihydrobenzo[1,2-b]furan (1.85 g,11.3 mmol), triethylamine (1.26 g, 12.4 mmol), 4-dimethylaminopyridine (0.07 g, 0.57 mmol), and tosyl chloride (2.58 g, 13.6 mmol). The reaction was warmed to 22° C. after two h and allowed to continue reaction for an additional 14 h. The reaction was extracted with ice water (2×~10 mL), saturated aqueous NaCl solution, dried with anhydrous $MgSO_4$, filtered, and concentrated in vacuo to afford a yellow solid. Silica gel chromatography [90:10 Hexane:EtOAc] of the solid material afforded the title compound (2.99 g, 83%) which was used without further purification.

Example 3

Preparation of 2,3-dihydro-3-(2-hydroxyethyl)benzo[b]furan;

To a stirred 0° C. solution of THF (~50 mL) containing LAH (0.86 g, 22.6 mmol) under $N_2$ atmosphere was added dropwise a THF solution of ethyl 2,3-dihydrobenzo[1,2-b]furan-3-acetate (2.50 g, 11.3 mmol). After complete addition the reaction was allowed to warm to 22° C. and stand for two

13 h. The reaction was cooled to 0° C. and treated sequentially with water (0.9 mL), 15% NaOH (0.9 mL), and water (2.7 mL). After stirring for 2 h the reaction was filtered through Celite and the filter cake washed with THF and $Et_2O$. The organic filtrate was dried with anhydrous $MgSO_4$, filtered, and concentrated in vacuo to afford a the title compound (1.85 g, >99%) as a yellow oil which was used without further purification.

Example 4

Preparation of ethyl 2,3-dihydrobenzo[b]furan-3-acetate:

To ethyl 4-(2-bromophenyloxy)but-2-enoate (6.10 g, 21.0 mmol) in benzene (200 mL) at reflux was added AIBN (0.07 g, 0.4 mmol) followed by dropwise addition of a benzene (~65 mL) solution containing tri-n-butyltin hydride (6.72 g, 23.1 mmol). After complete addition (one h) the reaction was refluxed an additional 2 h. The reaction was concentrated in vacuo and the residue treated with $Et_2O$ (~50 mL) and a 60% KF solution (~40 mL). The solution was stirred 14 h. The precipitate was removed by filtration and the $Et_2O$ phase decanted off. The remaining aqueous phase was extracted with $Et_2O$ (3×). The combined $Et_2O$ solutions were washed with saturated aqueous NaCl solution, dried with anhydrous $MgSO_4$, filtered, and concentrated in vacuo. Silica gel chromatography (95:5 Hexane:EtOAc) afforded the title compound (4.12 g, 88%).

Example 5

Preparation of ethyl 4-(2-bromophenyloxy)but-2-enoate:

To an acetone solution containing pulverized anhydrous $K_2CO_3$ (5.58 g, 40.5 mmol) and 2-bromophenol (5.0 g, 28.9 mmol) was added ethyl 4-bromocrotonate (6.69 g, 34.7 mmol). The mixture was stirred at 22° C. for 5 h and filtered. The filtrate was concentrated in vacuo and treated with 5% $NaHCO_3$ (~10 mL). The residue and aqueous phase were extracted with $CH_2Cl_2$ (3×). The combined organic extracts were dried with anhydrous $MgSO_4$, filtered, and concentrated in vacuo to afford the title compound (6.10 g, 74%) as a solid material which was used without further purification. 2,3-Dihydrobenzo[b]thiene type:

Example 6

Preparation of 1-[2-(2,3-dihydro-benzo[b]thien-3-yl)ethyl]-4-(3-methoxy-2-pyridinyl)-2-methylpiperazine hydrochloride To $CH_3CN$ (50 mL) was added 2,3-dihydro-3-benzo[b] thieneethanol tosylate (2.00 g, 6.0 mmol), 1-(3-methoxy-2-pyridinyl)-3-methylpiperazine (2.0 g, 9.7 mmol), anhydrous $K_2CO_3$ (2.48 g, 18.0 mmol), KI (0.05 g, 0.3 mmol), and tetra-n-butylammonium hydrogen sulfate (0.10 g, 0.3 mmol). The mixture was heated at reflux under $N_2$ atmosphere for 6 h and allowed to cool to 22° C. over 10 h. The reaction was concentrated in vacuo, several mL of $H_2O$ added and the reaction extracted with three portions of $CH_2Cl_2$. The combined organic extracts were washed with saturated aqueous NaCl solution, dried with anhydrous $K_2CO_3$, filtered, and concentrated in vacuo. Silica gel chromatography (98:2 $CH_2Cl_2$:MeOH) of the concentrate afforded the free base (1.60 g, 72%) which was treated with ethanolic HCl to yield the title compound (1.30 g, 67%, mp 219°–222° C.) after crystallization from EtOH/i-PrOH.

Anal. calcd. for $C_{21}H_{27}N_3O_1S_1/2HCl/0.3H_2O$: C, 56.33; H, 6.67; N, 9.39. Found: C, 53.57; H, 6.56; N, 9.37. DCI MS: $(M+H)^+$ m/e=370.

14

Example 7

Preparation of 1-[2-(2,3-dihydro-benzo[b]thien-3-yl) propyl]-4-(3-methoxy-2-pyridinyl)-2-methylpiperazine hydrochloride The title compound was prepared (48%, mp 167°–170° C.) in a manner analogous to the preparation of 1-[2-(2,3-dihydrobenzo[b]thien-3-yl)ethyl]-4-(3-methoxy-2-pyridinyl)-2-methylpiperazine hydrochloride (Example 6) by the reaction of 2,3-dihydro-3-benzo[b]-thienepropanol tosylate with 1-(3-methoxy-2-pyridinyl)-3-methylpiperazine.

Anal. calcd. for $C_{22}H_{29}N_3O_1S_1/2HCl/0.4H_2O$: C, 56.99; H, 6.92; N, 9.07. Found: C, 57.02; H, 6.66; N, 9.02. DCI MS: $(M+H)^+$ m/e=384.

Example 8

Preparation of 2,3-dihydro-3-benzo[b]thienepropanol tosylate

The title compound was prepared (6.71 g, 85%) in a manner analogous to the preparation of 2,3-dihydro-3-benzo[b]furanethanol tosylate (Example 2) by the reaction of 2,3-dihydro-3-benzo[b]thienepropanol with tosyl chloride.

Example 9

Preparation of 2,3-dihydro-3-benzo[b]thienepropanol

The title compound was prepared (4.42 g, >95%) in a manner analogous to the preparation of 2,3-dihydro-3-(2-hydroxyethyl)benzo[b]furan (Example 3) by the reaction of ethyl 2,3-dihydrobenzo[b]thiene-3-propanoate with LAH.

Example 10

Preparation of ethyl 2,3-dihydrobenzo[b]thiene-3-propanoate

An ethanol (400 mL) solution containing 2,3-dihydrobenzo[b]thiene-3-propanoic acid (8.8 g, 42.2 mmol) and $H_2SO_4$ (10 mL) was heated at reflux for ~40 h. The reaction was neutralized to a pH of 7 by the addition of 5N NaOH and concentrated in vacuo. The residue was dissolved in water and extracted with $CH_2Cl_2$ (3×). The combined organic phases were dried with $K_2CO_3$, filtered, and concentrated in vacuo. Silica gel chromatography (95:5 Hexane:EtOAc) of the concentrate afforded the title compound (5.37 g, 54%).

Example 11

Preparation of 2,3-dihydrobenzo[b]thiene-3-propanoic acid

A 6N HCl (50 mL) solution containing 2,3-dihydrobenzo[b]thiene-3-propanenitrile (1.0 g, 5.3 mmol) was heated at reflux for 24 h. The solvent was removed in vacuo to afford the title compound (1.1 g, >99%) as a yellow solid.

Example 12

Preparation of 2,3-dihydrobenzo[b]thiene-3-propanenitrile

A DMSO (35 mL) solution containing 2,3-dihydro-3-benzo[b]thieneethanol tosylate (5.60 g, 16.8 mmol) and KCN (3.28 g, 50.4 mmol) was heated at 60° C. for ~20 h. The reaction was transferred to a separatory funnel containing EtOAc (200 mL) and extracted with water (4×100 mL). The organic phase was washed with saturated aqueous NaCl, dried with $MgSO_4$, filtered, and concentrated in vacuo. Silica gel chromatography (90:10 Hexane:EtOAc) afforded the title compound (2.66 g, 84%).

Example 13

Preparation of 2,3-dihydro-3-benzo[b]thieneethanol tosylate

The title compound was prepared (11.47 g, 72%) in a manner analogous to the preparation of 2,3-dihydro-3-benzo[b]furanethanol tosylate (Example 2) by the reaction of 2,3-dihydro-3-benzo[b]thieneethanol with tosyl chloride.

Example 14
Preparation of 2,3-dihydro-3-(2-hydroxyethyl)benzo[b]thiene

The title compound was prepared (8.60 g, 91%) in a manner analogous to the preparation of 3-(2-hydroxyethyl)-2,3-dihydrobenzo[1,2-b]furan (Example 3) by the reaction of ethyl 2,3-dihydrobenzo[b]thiene-3-acetate with LAH.

Example 15
Preparation of ethyl 2,3-dihydrobenzo[b]thiene-3-acetate

The title compound was prepared (11.97 g, 62%) in a manner analogous to the preparation of ethyl 2,3-dihydrobenzo[1,2-b]furan-3-acetate (Example 4) by the reaction of ethyl 4-(2-bromophenylthio)but-2-enoate with tri-n-butyltin hydride.

Example 16
Preparation of ethyl 4-(2-bromophenylthio)but-2-enoate

The title compound was prepared (26.1 g, 82%) in a manner analogous to the preparation of ethyl 4-(2-bromophenyloxy)but-2-enoate (Example 5) by the reaction of 2-bromothiophenol with ethyl 4-bromocrotonate.

Example 17
Preparation of 1-[2-(2,3-dihydro-benzo[b]thien-3-yl)ethyl]-4-(3-methoxy-2-pyridinyl)piperazine hydrochloride To $CH_3CN$ (50 mL) was added 2,3-dihydro-3-benzo[b]thieneethanol tosylate (1.40 g, 4.2 mmol), 1-(3-methoxy-2-pyridinyl)piperazine (1.62 g, 8.2 mmol), anhydrous $K_2CO_3$ (1.74 g, 12.6 mmol), KI (0.03 g, 0.2 mmol), and tetra-n-butylammonium hydrogen sulfate (0.07 g, 0.2 mmol). The mixture was heated at reflux under $N_2$ atmosphere for 2 h. The reaction was concentrated in vacuo, $H_2O$ (~5 mL) added and the reaction extracted with two portions of $CH_2Cl_2$. The combined organic extracts were washed with saturated aqueous NaCl solution, dried with anhydrous $K_2CO_3$, filtered, and concentrated in vacuo. Silica gel chromatography (96:4 EtOAc:MeOH) of the concentrate afforded the free base (1.02 g, 68%) which was treated with ethanolic HCl to yield the title compound (1.12 g, 91%, mp 217°–220° C.).

Anal. calcd. for $C_{20}H_{25}N_3O_1S_1/2HCl/0.1H_2O$: C, 55.84; H, 6.38; N, 9.77. Found: C, 55.74; H, 6.66; N, 9.38. DCI MS: $(M+H)^+$ m/e=256

Example 18
Preparation of 1-[3-(2,3-dihydro-benzo[b]thien-3-yl)propyl]-4-(5-methoxy-4-pyrimidinyl)-2-methylpiperazine hydrochloride To DMF (5 mL) was added 2,3-dihydro-3-benzo[b]thienepropanol tosylate (0.76 g, 2.2 mmol), 1-(3-methoxy-2-pyrimidinyl)-3-methylpiperazine (0.91 g, 4.4 mmol), N-ethyldiisopropylamine (0.28 g, 2.2 mmol), KI (0.05 g, 0.3 mmol), and tetra-n-butylammonium hydrogen sulfate (0.04 g, 0.1 mmol). The mixture was heated at 50° C. under $N_2$ atmosphere for ~6 h. The reaction was concentrated in vacuo, 5% $NaHCO_3$ (~5 mL) added and the reaction extracted with four portions of $CH_2Cl_2$. The combined organic extracts were washed with saturated aqueous NaCl solution, dried with anhydrous $K_2CO_3$, filtered, and concentrated in vacuo. Silica gel chromatography (99:1 $CH_2Cl_2$:MeOH) of the concentrate afforded the free base (0.52 g, 62%) which was treated with ethanolic HCl to yield the title compound (0.80 g, 13%, mp 165°–169° C.) after crystallization from EtOH.

Anal. calcd. for $C_{21}H_{28}N_4O_1S_1/2HCl/0.3H_2O$: C, 54.50; H, 6.67; N, 12.11. Found: C, 54.59; H, 6.43; N, 12.26. DCI MS: $(M+H)^+$ m/e=385.

Example 19
Preparation of 1-[3-(2,3-dihydro-benzo[b]thien-3-yl)propyl]-4-(3-methoxy-2-pyridinyl)piperazine hydrochloride The title compound was prepared (1.23 g, 63%, mp 171°–173° C., crystallized from EtOH) in a manner analogous to the preparation of 1-[2-(2,3-dihydro-benzo[b]thien-3-yl)ethyl]-4-(3-methoxy-2-pyridinyl)piperazine hydrochloride (Example 17) by the reaction of 2,3-dihydro-3-benzo[b]thienepropanol tosylate with 1-(3-methoxy-2-pyridinyl)piperazine.

Anal. calcd. for $C_{21}H_{27}N_3O_1S_1/2HCl/0.5H_2O$: C, 55.88; H, 6.70; N, 9.31. Found: C, 55.68; H, 6.74; N, 9.06. DCI MS: $(M+H)^+$ m/e=370.

Benzo[b]furan type:

Example 20
Preparation of 1-[3-(5-fluorobenzo[b]furan-3-yl)propyl]-4-(3-methoxy-2-pyridinyl)piperazine hydrochloride The title compound was prepared (0.93 g, 74%, mp 182°–184° C.) in a manner analogous to the preparation of 1-[2-(2,3-dihydrobenzo[b]thien-3-yl)ethyl]-4-(3-methoxy-2-pyridinyl)piperazine hydrochloride (Example 17) by the reaction of 5-fluoro-3-benzo[b]furanpropanol tosylate with 1-(3-methoxy-2-pyridinyl)piperazine.

Anal. calcd. for $C_{21}H_{24}FN_3O_2/1.9HCl$: C, 57.50; H, 5.96; N, 9.58. Found: C, 57.58; H, 5.90; N, 9.61. DCI MS: $(M+H)^+$ m/e=.

Example 21
Preparation of 5-fluoro-3-benzo[b]furanpropanol tosylate

To a refluxing benzene (1000 mL) solution containing 5-(2-bromo-4-fluorophenoxy)-pent-3-yne-1-ol tosylate (8.39 g, 19.6 mmol) was added a catalytic amount of AIBN (0.02 mole %) followed by dropwise addition of n-$Bu_3SnH$ (11.4 g, 39.3 mmol). After the addition was complete the reaction was heated several h and additional n-$Bu_3SnH$ (8.7 g, 30 mmol) added at reflux over 8 h. After allowing the reaction to cool to 22° C. 38% KF (aq) (20 mL) was added and allowed to stir ~16 h. The reaction mixture was filtered and the organic layer decanted away. The aqueous phase was washed with $Et_2O$ (3×50 mL) and combined with the organic decantate. The organic phase was dried with $MgSO_4$, filtered, concentrated in vacuo, and preabsorbed on silica gel (20 g). Silica gel chromatography (9:1 Hexane:EtOAc) yield a solid material (5.80 g) which consisted of a mixture of the title compound (20%) and its exocyclic isomer (80%). This mixture was dissolved in chlorobenzene (100 mL) containing $(Ph_3P)_3RhCl$ (0.032 g) and heated at reflux for 4 h. Silica gel chromatography (9:1 to 4:1 Hexane:EtOAc gradient) afforded the title compound (5.27 g, 77%).

Example 22
Preparation of 5-(2-bromo-4-fluorophenoxy)pent-3-yne-1-ol tosylate To MeOH (140 mL) solution containing KOH (4.73 g, 84.3 mmol) at 22° C. was added 2-bromo-4-fluorophenol (16.09 g, 84.2 mmol) and 2-pentyne-1,5-diol ditosylate (11.47 g, 28.1 mmol). After stirring 20 h acetic acid (3.5 mL) was added and the reaction stirred 1 h. The reaction was concentrated in vacuo and the residue extracted with $CH_2Cl_2$ (75 mL) and saturated $K_2CO_3$ (75 mL). The organic phase was separated and washed with saturated $K_2CO_3$. The aqueous phase was washed with $CH_2Cl_2$ (2×30 mL). The combined $CH_2Cl_2$ layers were dried with dried with $MgSO_4$, filtered, concentrated in vacuo. Silica gel chromatography (9:1 Hexane:EtOAc) yielded the title compound as a viscous oil (8.39 g, 70%).

Example 23
Preparation of pent-2-yne-1,5-diol ditosylate

A THF (~800 mL) solution containing pent-2-yne-1,5-diol (21.4 g, 0.21 mole), tosic anhydrinde (150.12 g, 0.46 mole) and 2,4,6-collidine (56.94 g, 0.47 mole) was stirred for 7 days. The reaction was filtered and concentrated in vacuo. Silica gel chromatography ($CH_2Cl_2$) of the concentrate afforded the title compound (67.29 g, 77%).

Example 24
Preparation of 2-pentyne-1,5-diol $CaCO_3$ (0.52 g, 0.005 mole), water (~10 mL), formaldehyde (60 mL of 37% aq solution), 3-butyn-1-ol (37.04 g, 0.53 mole) and freshly prepared CuOH (from 8.46 g CuCl) were heated at reflux for 90 h while under $N_2$ atmosphere. The reaction was filtered and the filtrate distilled to yield the title compound (25.74 g, 49%; bp 105°–110° C. @ 0.05 mm Hg).

Example 25
Preparation of 1-[3-(5-chlorobenzo[b]furan-3-yl)propyl]-4-(3-methoxy-2-pyridinyl)piperazine hydrochloride To $CH_3CN$ (~13 mL) was added 5-fluoro-3-benzo[b]furanpropanol tosylate (0.98 g, 2.7 mmol), 1-(3-methoxy-2-pyridinyl)piperazine (0.53 g, 2.7 mmol), and N-ethyldiisopropylamine (1.04 g, 8.0 mmol). The solution was heated at reflux under $N_2$ atmosphere for 8 h. The reaction was concentrated in vacuo and the residue dissolved in $CH_2Cl_2$. After aqueous 10% $K_2CO_3$ extraction the organic phase was dried with anhydrous $MgSO_4$, filtered, and concentrated in vacuo. Silica gel chromatography (95:5 $CH_2Cl_2$:MeOH) of the concentrate afforded the free base (0.63 g, 61%) which was treated with ethanolic HCl to yield the title compound (0.54 g, 78%, mp 211°–213° C.).

Anal. calcd. for $C_{21}H_{24}N_3ClO_2/1.02HCl$: C, 59.62; H, 5.97; N, 9.94. Found: C, 59.30; H, 5.88; N, 9.87. DCI MS: $(M+H)^+$ m/e=386.

Example 26
Preparation of 5-chloro-3-benzo[b]furanpropanol tosylate

The title compound was prepared (2.17 g, 57%) in a manner analogous to the preparation of 5-fluoro-3-benzo[b]furanpropanol tosylate (Example 21) by the reaction of 5-(2-bromo-4-chlorophenoxy)pent-3-yn-1-ol tosylate with n-$Bu_3SnH$.

Example 27
Preparation of 1-[3-(5-chlorobenzo[b]furan-3-yl)propyl]-4-(5-methoxy-4-pyrimidinyl)-2-methylpiperazine hydrochloride The title compound was prepared (0.24 g, 81%, mp 199°–200° C.) in a manner analogous to the preparation of 1-[3-(5-chlorobenzo[b]furan-3-yl)propyl]-4-(3-methoxy-2-pyridinyl)piperazine (Example 25) by the reaction of 5-chloro-3-benzo[b]furan)propanol tosylate with 1-(3-methoxy-2-pyridinyl)-3-methylpiperazine.

Anal. calcd. for $C_{21}H_{25}ClN_4O_2/1.5HCl$: C, 55.37; H, 5.87; N, 12.30. Found: C, 55.33; H, 5.82; N, 12.20. DCI MS: $(M+H)^+$ m/e=401.

Example 28
Preparation of 1-[3-(benzo[b]furan-3-yl)propyl]-4-(5-methoxy-4-pyrimidinyl)-3-methylpiperazine hydrochloride The title compound was prepared (0.60 g, 61%, mp 120°–125° C. after crystallization from EtOH) in a manner analogous to the preparation of 1-[2-(2,3-dihydro-benzo[b]thiene-3-yl)propyl]-4-(5-methoxy-4-pyrimidinyl)-2-methylpiperazine (Example 18) by the reaction of 3-benzo[b]furanpropanol tosylate with 1-(5-methoxy-4-pyrimidinyl)-2-methylpiperazine.

Anal. calcd. for $C_{21}H_{26}N_4O_2/2.3HCl/1.5H_2O$: C, 52.84; H, 6.61; N, 11.74. Found: C, 53.24; H, 6.62; N, 11.35. DCI MS: $(M+H)^+$ m/e=367.

Example 29
Preparation of 1-[3-(5-methylbenzo[b]furan-3-yl)propyl]-4-(3-methoxy-2-pyridinyl)piperazine hydrochloride The title compound was prepared (0.66 g, 92%, mp 163°–165° C.) in a manner analogous to the preparation of 1-[3-(5-chlorobenzo[b]furan-3-yl)propyl]-4-(3-methoxy-2-pyridinyl)piperazine (Example 25) by the reaction of 5-methyl-3-benzo[b]furan)propanol tosylate with 1-(3-methoxy-2-pyridinyl)piperazine.

Anal. calcd. for $C_{22}H_{27}N_3O_2/1.1HCl/0.3H_2O/0.13EtOH$: C, 64.12; H, 7.13; N, 10.08. Found: C, 64.18; H, 7.30; N, 9.71. DCI MS: $(M+H)^+$ m/e=366.

Example 30
Preparation of 1-[3-(5-methylbenzo[b]furan-3-yl)propyl]-4-(5-methoxy-4-pyrimidinyl)-2-methylpiperazine hydrochloride The title compound was prepared (0.34 g, 74%, mp 185.5°–187.5° C. after crystallization from EtOH) in a manner analogous to the preparation of 1-[3-(5-chlorobenzo[b]furan-3-yl)propyl]-4-(3-methoxy-2-pyridinyl)piperazine (Example 25) by the reaction of 5-methyl-3-benzo[b]furan)propanol tosylate with 1-(5-methoxy-4-pyrimidinyl)-3-methylpiperazine.

Anal. calcd. for $C_{22}H_{28}N_4O_2/1.5HCl$: C, 60.73; H, 6.84; N, 12.88. Found: C, 60.84; H, 6.91; N, 12.70. DCI MS: $(M+H)^+$ m/e=381.

Example 31
Preparation of 1-[3-(benzo[b]furan-3-yl)propyl]-4-(3-methoxy-2-pyridinyl)piperazine hydrochloride The title compound was prepared (0.73 g, 91%, mp 179.5°–182° C.) in a manner analogous to the preparation of 1-[3-(5-chlorobenzo[b]furan-3-yl)propyl]-4-(3-methoxy-2-pyridinyl)piperazine (Example 25) by the reaction of 3-benzo[b]furanpropanol tosylate with 1-(3-methoxy-2-pyridinyl)piperazine.

Anal. calcd. for $C_{21}H_{25}N_3O_2/1.6HCl$: C, 61.56; H, 6.55; N, 10.26. Found: C, 61.57; H, 6.51; N, 10.23. DCI MS: $(M+H)^+$ m/e=352.

$^1$H NMR: ($D_6$-DMSO) δ 2.16 (m, 2H), 2.75 (t, 2H, J=7.4 Hz), 3.1–3.3 (m, 6H), 3.56 (d, 2H, J=12.3 Hz), 3.83 (s, 3H), 4.03 (d, 2H, J=13.6 Hz), 7.00 (dd, 1H), 7.25–7.40 (m, 3H), 7.57 (d, 1H, J=7.5 Hz), 7.69 (d, 1H, J=7.2 Hz), 7.82 (dd, 1H), 7.89 (s, 1H), 11.0 (s, 1H).

Example 32
Preparation of 1-[3-(benzo[b]furan-3-yl)propyl]-4-(5-methoxy-4-pyrimidinyl-2-methylpiperazine hydrochloride The title compound was prepared (0.34 g, 49%, mp 195°–197° C. after crystallization from EtOH) in a manner analogous to the preparation of 1-[3-(benzo[b]furan-3-yl)propyl]-4-(5-methoxy-4-pyrimidinyl)-3-methylpiperazine hydrochloride (Example 28) by the reaction of 3-benzo[b]furanpropanol tosylate with 1-(5-methoxy-4-pyrimidinyl)-3-methylpiperazine.

Anal. calcd. for $C_{21}H_{26}N_4O_2/2.0HCl/0.8H_2O$: C, 55.59; H, 6.58; N, 12.35. Found: C, 55.49; H, 6.18; N, 12.26. DCI MS: $(M+H)^+$ m/e=367.

Example 33
Preparation of 1-[2-(benzo[b]furan-3-yl)ethyl]-4-(3-methoxy-2-pyridinyl)piperazine hydrochloride The title compound was prepared (1.75 g, 91%, mp 140°–153° C. after crystallization from EtOH) in a manner analogous to the preparation of 1-[3-(benzo[b]furan-3-yl)propyl]-4-(5-methoxy-4-pyrimidinyl)-3-methylpiperazine hydrochloride (Example 28) by the reaction of 3-benzo[b]furanethanol tosylate with 1-(3-methoxy-2-pyridinyl)piperazine.

Anal. calcd. for $C_{20}H_{23}N_3O_2/2.0HCl/0.2H_2O$: C, 58.04; H, 6.19; N, 10.16. Found: C, 58.19; H, 6.42; N, 10.39. DCI MS: $(M+H)^+$ m/e=338.

Example 34
Preparation of ethyl benzo[b]furan-3-acetate

A toluene solution under $N_2$ atmosphere containing ethyl 2,3-dihydrobenzo[b]furan-3-acetate (9.80 g, 47.6 mmol) and 2,3-dichloro-5,6-dicyano-1,4-benzoquinone (DDQ) (12.97 g, 57.1 mmol) was heated at reflux for ~8 h. The reaction was filtered and the filtrate concentrated in vacuo. Silica gel chromatography (97:3 Hexane:EtOAc) of the residue afforded the title compound (7.24 g, 75%) as an orange oil.

Example 35
Preparation of 3-benzo[b]furanethanol tosylate

The title compound was prepared by first reducing the compound of example 34 with $LiAlH_4$ (cf. Example 14) and subsequent treatment with TsCl (cf. Example 13).

Example 36
Preparation of 1-[2-(5-chlorobenzo[b]furan-3-yl)ethyl]-4-(3-methoxy-2-pyridinyl)piperazine hydrochloride The title compound was prepared (0.55 g, 63%, mp 217°–220° C.) in a manner analogous to the preparation of 1-[3-(5-chlorobenzo[b]furan-3-yl)propyl]-4-(3-methoxy-2-pyridinyl)piperazine (Example 25) by the reaction of 5-chloro-3-benzo[b]furanethanol tosylate with 1-(3-methoxy-2-pyridinyl)piperazine.

Anal. calcd. for $C_{20}H_{22}ClN_3O_2/1.5$ HCl/1.0 EtOH/0.1 $H_2O$: C, 55.70; H, 6.32; N, 8.86. Found: C, 55.38; H, 5.90; N, 8.73. DCI MS: $(M+H)^+$ m/e=372.

Example 37
Preparation of 1-[3-(5-fluorobenzo[b]furan-3-yl)propyl]-4-(5-methoxy-4-pyrimidinyl)piperazine hydrochloride The title compound was prepared (0.31 g, 87%, mp 196°–198° C.) in a manner analogous to the preparation of 1-[3-(5-fluorobenzo[b]furan-3-yl)propyl]-4-(3-methoxy-2-pyridinyl)piperazine hydrochloride (Example 20) by the reaction of 5-fluoro-3-benzo[b]furanpropanol tosylate with 1-(5-methoxy-4-pyrimidinyl)piperazine.

Anal. calcd. for $C_{20}H_{23}FN_4O_2/1.3HCl$: C, 57.49; H, 5.86; N, 13.41. Found: C, 57.19; H, 5.82; N, 13.16. DCI MS: $(M+H)^+$ m/e=371.

$^1H$ NMR: ($d_6$-DMSO) δ 2.1 (m, 2H), 2.7 (t, 2H), 3.0–3.6 (m, 8H), 4.0 (s, 3H), 4.6 (d, 2H), 7.2 (t, 1H), 7.5–7.6 (m, 2H), 8.0 (s, 1H), 8.2 (s, 1H), 8.4 (s, 1H), 11.1 (bs, 1H).

Example 38
Preparation of 1-[3-(benzo[b]furan-3-yl)propyl]-4-(5-methoxy-4-pyrimidinyl)piperazine hydrochloride The title compound was prepared (0.24 g, 51%, mp 189°–190° C. after crystallization from EtOH/i-PrOH) in a manner analogous to the preparation of 1-[3-(benzo[b]furan-3-yl)propyl]-4-(5-methoxy-4-pyrimidinyl)-3-methylpiperazine hydrochloride (Example 28) by the reaction of 3-benzo[b]furanpropanol tosylate with 1-(5-methoxy-4-pyrimidinyl)piperazine.

Anal. calcd. for $C_{20}H_{24}N_4O_2/2.0HCl/0.08H_2O/0.1i$-PrOH: C, 56.34; H, 6.28; N, 12.95. Found: C, 56.51; H, 6.03; N, 12.95. DCI MS: $(M+H)^+$ m/e=353.

Example 39
Preparation of 1-[3-(5-methoxybenzo[b]furan-3-yl)propyl]-4-(5-methoxy-4-pyrimidinyl)piperazine hydrochloride The title compound was prepared (0.31 g, 87%, mp 196°–198° C.) in a manner analogous to the preparation of 1-[3-(5-fluorobenzo[b]furan-3-yl)propyl]-4-(3-methoxy-2-pyridinyl)piperazine hydrochloride (Example 20) by the reaction of 5-methoxy-3-benzo[b]furanpropanol tosylate with 1-(5-methoxy-4-pyrimidinyl)piperazine. 5-Methoxy-3-benzo[b]furanpropanol tosylate was prepared from 2-bromo-4-methoxyphenol in a manner analogous to the preparation of 5-fluoro-3-benzo[b]furanpropanol tosylate (Example 21).

Anal. calcd. for $C_{21}H_{26}N_4O_3/1.05HCl$: C, 59.95; H, 6.48; N, 13.32. Found: C, 59.85; H, 6.44; N, 13.21. DCI MS: $(M+H)^+$ m/e=383.

Example 40
Preparation of 1-[3-(5-methoxybenzo[b]furan-3-yl)propyl]-4-(3-ethoxy-2-pyridinyl)piperazine hydrochloride The title compound was prepared (0.69 g, 75%, mp 174°–176° C.) in a manner analogous to the preparation of 1-[3-(5-methoxybenzo[b]furan-3-yl)propyl]-4-(5-methoxy-4-pyrimidinyl)piperazine hydrochloride (Example 39) by the reaction of 5-methoxy-3-benzo[b]furanpropanol tosylate with 1-(3-methoxy-2-pyridinyl)piperazine.

Anal. calcd. for $C_{22}H_{27}N_3O_3/1.3HCl$: C, 61.62; H, 6.66; N, 9.80. Found: C, 61.53; H, 6.67; N, 9.63. DCI MS: $(M+H)^+$ m/e=382.

Benzo[b]thiene type:

Example 41
Preparation of 1-[3-(benzo[b]thien-3-yl)propyl]-4-(3-methoxy-2-pyridinyl)-2-methylpiperazine hydrochloride The title compound was prepared (1.04 g, 70%, mp 189°–193° C.) in a manner analogous to the preparation of 1-[2-(2,3-dihydro-benzo[b]thien-3-yl)propyl]-4-(3-methoxy-2-pyridinyl)-2-methylpiperazine hydrochloride (Example 7) by the reaction of 3-benzo[b]thienpropanol tosylate with 1-(3-methoxy-2-pyridinyl)-3-methylpiperazine.

Anal. calcd. for $C_{22}H_{27}N_3OS/2.0HCl/0.5H_2O$: C, 57.02; H, 6.53; N, 9.07. Found: C, 57.23; H, 6.38; N, 9.13. DCI MS: $(M+H)^+$ m/e=382.

Example 42
Preparation of 3-benzo[b]thienepropanol tosylate

The title compound was prepared in a manner analogous to the preparation of 2,3-dihydro-3-benzo[b]thienepropanol tosylate (Example 8) by the reaction of 3-benzo[b]thienepropanol with tosyl chloride.

Example 43
Preparation of 3-benzo[b]thienepropanol

The title compound was prepared in a manner analogous to the preparation of 2,3-dihydro-3-benzo[b]thienepropanol (Example 9) by the reaction of ethyl benzo[b]thiene-3-propanoate with LAH.

Example 44
Preparation of ethyl benzo[b]thiene-3-propanoate

The title compound was prepared in a manner analogous to the preparation of ethyl 2,3-dihydro-3-benzo[b]thienepropanoate (Example 10) by the esterification of benzo[b]thiene-3-propanoic acid with ethanol.

Example 45
Preparation of benzo[b]thiene-3-propanoic acid

The title compound was prepared in a manner analogous to the preparation of 2,3-dihydro-3-benzo[b]thienepropanoic acid (Example 11) by the hydrolysis of benzo[b]thiene-3-propanenitrile with HCl.

Example 46
Preparation of benzo[b]thiene-3-propanenitrile

The title compound was prepared in a manner analogous to the preparation of 2,3-dihydro-3-benzo[b]thienepropanenitrile (Example 12) by the reaction of benzo[b]thiene-3-ethanol tosylate with KCN.

Example 47
Preparation of benzo[b]thiene-3-ethanol tosylate

The title compound was prepared in a manner analogous to the preparation of 2,3-dihydrobenzo[b]thiene-3-ethanol tosylate (Example 13) by the reaction of 3-(2-hydroxyethyl)benzo[b]thiene with tosyl chloride.

Example 48
Preparation of 3-(2-hydroxyethyl)benzo[b]thiene

The title compound was prepared in a manner analogous to the preparation of 2,3-dihydro-3-(2-hydroxyethyl)benzo[b]thiene (Example 14) by the reaction of ethyl benzo[b]thiene-3-acetate with LAH.

Example 49
Preparation of ethyl benzo[b]thien-3-acetate

A toluene (~100 mL) solution containing ethyl 2,3-dihydrobenzo[b]thien-3-acetate (8.46 g, 38.1 mmol) and 2,3-dichloro-5,6-dicyano-1,4-benzoquinone (10.38 g, 45.7 mmol) was heated at reflux ~20 h. The reaction was filtered and concentrated in vacuo. Silica gel chromatography (98:2 Hexane:EtOAc) of the concentrate afforded the title compound (3.94 g, 47%).

Example 50
Preparation of 1-[3-(benzo[b]thien-3-yl)propyl]-4-(5-methoxy-4-pyrimidinyl)-2-methylpiperazine hydrochloride The title compound was prepared (0.80 g, 85%, mp 200°–205° C.) in a manner analogous to the preparation of 1-[3-(benzo[b]thien-3-yl)propyl]-4-(3-methoxy-2-pyridinyl)-2-methylpiperazine hydrochloride (Example 41) by the reaction of 3-benzo[b]thienepropanol tosylate with 1-(5-methoxy-4-pyrimidinyl)-3-methylpiperazine.

Anal. calcd. for $C_{21}H_{26}N_4OS/2.0HCl/0.5H_2O$: C, 54.31; H, 6.30; N, 12.07. Found: C, 54.34; H, 6.06; N, 12.00. DCI MS: $(M+H)^+$ m/e=383.

Example 51
Preparation of 1-[3-(benzo[b]thien-3-yl)propyl]-4-(5-methoxy-4-pyrimidinyl)-3-methylpiperazine hydrochloride The title compound was prepared (0.44 g, 62%, mp 183°–186° C.) in a manner analogous to the preparation of 1-[3-(benzo[b]thien-3-yl)propyl]-4-(3-methoxy-2-pyridinyl)-2-methylpiperazine hydrochloride (Example 41) by the reaction of 3-benzo[b]thienepropanol tosylate with 1-(5-methoxy-4-pyrimidinyl)-2-methylpiperazine.

Anal. calcd. for $C_{21}H_{26}N_4OS/2.3HCl/1.0H_2O$: C, 52.07; H, 6.30; N, 11.57. Found: C, 51.80; H, 5.91; N, 11.48. DCI MS: $(M+H)^+$ m/e=383.

Example 52
Preparation of 1-[3-(5-fluorobenzo[b]thien-3-yl)propyl]-4-(5-methoxy-4-pyrimidinyl)piperazine hydrochloride The title compound was prepared (0.16 g, 62%, mp 174.5°–176° C.) in a manner analogous to the preparation of 1-[3-(benzo[b]thien-3-yl)propyl]-4-(3-methoxy-2-pyridinyl)-2-methylpiperazine hydrochloride (Example 41) by the reaction of 3-benzo[b]thienepropanol tosylate with 1-(5-methoxy-4-pyrimidinyl)piperazine.

Anal. calcd. for $C_{20}H_{23}FN_4OS/1.2HCl$: C, 55.83; H, 5.67; N, 13.02. Found: C, 55.87; H, 5.87; N, 13.24. DCI MS: $(M+H)^+$ m/e=387.

Example 53
Preparation of 3-(5-fluorobenzo[b]thiene)propanol tosylate

The title compound was prepared in a manner analogous to the preparation of 3-benzo[b]thienepropanol tosylate (Example 42) by the reaction of 5-fluorobenzo[b]thiene-3-propanol with tosyl chloride. 5-Fluorobenzo[b]thiene-3-propanol was prepared from the LAH reduction of t-butyl 5-fluorobenzo[b]thiene-3-propanoate.

Example 54
Preparation of t-butyl 5-fluorobenzo[b]thiene-3-propanoate

To a THF (~175 mL) solution containing t-butyl acetate (10.78 g, 92.8 mmol) at −78° C. was added lithium diisopropylamide (LDA) (9.92 g, 92.6 mmol). After stirring for 15 min 3-bromomethyl-5-fluorobenzo[b]thien (21.64 g, 88.3 mmol) dissolved in THF was added dropwise and the reaction allowed to warm to −25° C. After 90 min at −25° C. saturated $NH_4Cl$(aq) (5 mL) was added. Water was added and the THF layer separated and removed. The aqueous phase was washed with $Et_2O$ (~150 mL) and the $Et_2O$ and THF layers combined. The combined organic phases were dried with $MgSO_4$, filtered, and concentrated in vacuo. Silica gel chromatography (97:3 Hexane/EtOAc) of the concentrate afforded the title compound (20.91 g, 84%) as an amber oil.

Example 55
Preparation of 1-[3-(5-fluorobenzo[b]thien-3-yl)propyl]-4-(5-methoxy-4-pyrimidinyl)-3-methylpiperazine hydrochloride The title compound was prepared (0.28 g, 23%, mp 173°–173.5° C.) in a manner analogous to the preparation of 1-[3-(5-fluorobenzo[b]thien-3-yl)propyl]-4-(5-methoxy-4-pyrimidinyl)piperazine (Example 52) by the reaction of 5-fluoro-3-benzo[b]thienpropanol tosylate with 1-(5-methoxy-4-pyrimidinyl)-2-methylpiperazine.

Anal. calcd. for $C_{21}H_{25}FN_4OS/1.2HCl$: C, 56.77; H, 5.94; N, 12.61. Found: C, 56.86; H, 5.98; N, 12.28. DCI MS: $(M+H)^+$ m/e=401.

Example 56
Preparation of 1-[3-(benzo[b]thien-3-yl)propyl]-4-(3-methoxy-2-pyridinyl)piperazine fumarate The title compound was prepared (1.03 g, 52%, mp 167°–168° C.) in a manner analogous to the preparation of 1-[3-(benzo[b]thien-3-yl)propyl]-4 -(3-methoxy-2-pyridinyl)-2-methylpiperazine hydrochloride (Example 41) by the reaction of 3-benzo[b]thienepropanol tosylate with 1-(3-methoxy-2-pyridinyl)piperazine.

Anal. calcd. for $C_{21}H_{25}N_3OS/1.0C_4H_4O_4$: C, 62.09; H, 6.04; N, 8.69. Found: C, 61.99; H, 5.96; N, 8.66. DCI MS: $(M+H)^+$ m/e=.

Example 57
Preparation of 1-[2-(benzo[b]thien-3-yl)ethyl]-4-(3-methoxy-2-pyridinyl)piperazine hydrochloride The title compound was prepared (0.63 g, 56%, mp 208°–215° C.) in a manner analogous to the preparation of 1-[3-(benzo[b]thien-3-yl)propyl]-4-(3-methoxy-2-pyridinyl)-2-methylpiperazine hydrochloride (Example 41)

by the reaction of 3-benzo[b]thieneethanol tosylate (Example 47) with 1-(3-methoxy-2-pyridinyl)piperazine.

Anal. calcd. for $C_{20}H_{23}N_3OS/2.0HCl/0.5EtOH/0.1H_2O$: C, 55.90; H, 6.30; N, 9.32. Found: C, 55.56; H, 6.38; N, 9.63. DCI MS: $(M+H)^+$ m/e=354.

Example 58
Preparation of 1-[2-(benzo[b]thien-3-yl)ethyl]-4-(3-methoxy-2-pyridinyl)-2-methylpiperazine hydrochloride The title compound was prepared (1.39 g, 85%, mp 197°–200° C.) in a manner analogous to the preparation of 1-[3-(benzo[b]thien-3-yl)propyl]-4-(3-methoxy-2-pyridinyl)-2-methylpiperazine hydrochloride (Example 41) by the reaction of 3-benzo[b]thieneethanol tosylate (Example 47) with 1-(3-methoxy-2-pyridinyl)-3-methylpiperazine.

Anal. calcd. for $C_{21}H_{25}N_3OS/1.8HCl/0.3H_2O$: C, 57.52; H, 6.30; N, 9.59. Found: C, 57.56; H, 6.24; N, 9.54. DCI MS: $(M+H)^+$ m/e=368.

Example 59
Preparation of 1-[3-(benzo[b]thien-3-yl)propyl]-4-(5-methoxy-4-pyrimidinyl)piperazine hydrochloride The title compound was prepared (1.03 g, 74%, mp 209°–212° C.) in a manner analogous to the preparation of 1-[3-(benzo[b]thien-3-yl)propyl]-4-(3-methoxy-2-pyridinyl)-2-methylpiperazine hydrochloride (Example 41) by the reaction of 3-benzo[b]thienepropanol tosylate with 1-(5-methoxy-4-pyrimidinyl)piperazine.

Anal. calcd. for $C_{20}H_{24}N_4OS/2.25HCl/0.25H_2O$: C, 52.80; H, 5.93; N, 12.32. Found: C, 52.92; H, 5.72; N, 12.28. DCI MS: $(M+H)^+$ m/e=369.

Example 60
Preparation of 1-[3-(benzo[b]thien-3-yl)propyl]-4-(5-chloro-3-methoxy-2-pyridinyl)-2-methylpiperazine hydrochloride The title compound was prepared (0.17 g, 42%, mp 214°–216° C.; crystallized from EtOH) in a manner analogous to the preparation of 1-[3-(benzo[b]thien-3-yl)propyl]-4-(3-methoxy-2-pyridinyl)-2-methylpiperazine hydrochloride (Example 41) by the reaction of 3-benzo[b]thienepropanol tosylate with 1-(5-chloro-3-methoxy-2-pyridinyl)-3-methylpiperazine.

Anal. calcd. for $C_{22}H_{26}ClN_3OS/1.0HCl/0.1H_2O$: C, 58.18; H, 6.04; N, 9.26. Found: C, 58.08; H, 5.77; N, 9.16. DCI MS: $(M+H)^+$ m/e=416.

Example 61
Preparation of 1-(5-chloro-3-methoxy-2-pyridinyl)-3-methylpiperazine 2-Bromo-5-chloro-3-methoxypyridine (0.50 g, 2.3 mmol) and 2-methylpiperazine (11.27 g, 11.3 mmol) were heated in a Parr steel reaction vessel at 100° C. for 24 h. After allowing to cool to 22° C. the solid mass was dissolved in a minimal amount of 5% aq $NaHCO_3$ and extracted with $CH_2Cl_3$. The organic phase was extracted with sat. NaCl solution, dried with $K_2CO_3$, filtered, and concentrated in vacuo. Silica gel chromatography (95:5:0.5 $CH_2Cl_2$:MeOH:$NH_4OH$) of the concentrate afforded the title compound (0.47 g, 87%).

Example 62
Preparation of 2-bromo-5-chloro-3-methoxypyridine

To a DMF (60 mL) solution containing 2-bromo-5-chloro-3-hydroxypyridine (19.95 g, 95.7 mmol) at 0° C. was added NaH (2.53 g, 105.3 mmol) portion wise. After the cessation of $H_2$ evolution, $CH_3I$ (14.26 g, 100.5 mmol) was added dropwise and the reaction stirred ~16 h. Water (1.9 mL) was added and the solvent removed under reduced pressure. The concentrate was triturated with 5 portions of $CH_2Cl_2$. The combined organic phases were washed with sat. NaCl solution, dried with $K_2CO_3$, filtered, and concentrated in vacuo. Silica gel chromatography (95:5 Hexane:EtOAc) of the concentrate afforded the title compound.

Example 63
Preparation of 1-[3-(5-fluorobenzo[b]thien-3-yl)propyl]-4-(5-methoxy-4-pyrimidinyl)-2-methylpiperazine hydrochloride The title compound was prepared (0.49 g, 91%, mp 187°–187.5° C.) in a manner analogous to the preparation of 1-[3-(5-fluorobenzo[b]thien-3-yl)propyl]-4-(5-methoxy-4-pyrimidinyl)piperazine (Example 52) by the reaction of 5-fluoro-3-benzo[b]thienepropanol tosylate with 1-(5-methoxy-4-pyrimidinyl)-3-methylpiperazine.

Anal. calcd. for $C_{21}H_{25}FN_4OS/1.1HCl$: C, 57.24; H, 5.97; N, 12.72. Found: C, 57.26; H, 5.96; N, 12.69. DCI MS: $(M+H)^+$ m/e=401.

Example 64
Preparation of 1-[2-(benzo[b]thien-3-yl)ethyl]-4-(5-methoxy-4-pyrimidinyl)-3-methylpiperazine hydrochloride The title compound was prepared (0.20 g, 24%, mp 140°–144° C.) in a manner analogous to the preparation of 1-[3-(benzo[b]thien-3-yl)propyl]-4-(3-methoxy-2-pyridinyl)-2-methylpiperazine hydrochloride (Example 41) by the reaction of 3-benzo[b]thieneethanol tosylate (Example 47) with 1-(5-methoxy-4-pyrimidinyl)-2-methylpiperazine.

Anal. calcd. for $C_{20}H_{24}N_4OS/2.0HCl/2.2H_2O$: C, 49.94; H, 6.37; N, 11.65. Found: C, 49.68; H, 6.12; N, 11.52. DCI MS: $(M+H)^+$ m/e=369.

Example 65
Preparation of 1-[3-(5-cyanobenzo[b]thien-3-yl)propyl]-4-(5-methoxy-4-pyrimidinyl)piperazine hydrochloride To a solution of anhydrous 1,4-dioxane containing 1-[3-(5-aminocarbonylbenzo[b]thien-3-yl)propyl]-4-(5-methoxy-4-pyrimidinyl)piperazine (0.16 g, 0.39 mmol) and anhydrous pyridine (0.06 g, 0.51 mmol) at 0° C. was added dropwise trifluoroacetic anhydride (0.10 g, 0.50 mmol). After stirring for 15 min at 0° C. the reaction was allowed to warm to 23° C. and stir an additional 3 h. Water was added and the reaction extracted with $CH_2Cl_2$. The combined organic extracts were washed with $K_2CO_3$ (aq), dried with $MgSO_4$, filtered, and concentrated in vacuo to afford the free base (0.07 g, 47%) of the title compound. Treatment of the free base with ethanolic HCl afforded the title compound (0.06 g, 69%).

Anal. calcd. for $C_{21}H_{23}N_5OS/2.5hcl/0.2H_2O$: C, 51.66; H, 5.35; N, 14.34. Found: C, 51.93; H, 5.72; N, 13.94. DCI MS: $(M+H)^+$ m/e=394.

Example 66
Preparation of 1-[3-(5-aminocarbonylbenzo[b]thien-3-yl)propyl]-4-(5-methoxy-4-pyrimidinyl)piperazine The title compound was prepared (0.20 g, 37%, mp 169°–170° C.) in a manner analogous to the preparation of 1-[3-(5-fluorobenzo[b]thien-3-yl)propyl]-4-(5-methoxy-4-pyrimidinyl)piperazine (Example 52) by the reaction of 3-(3-hydroxypropyl)benzo[b]thiene-5-carboxamide tosylate with 1-(5-methoxy-4-pyrimidinyl)piperazine.

Anal. calcd. for $C_{21}H_{25}N_5O_2S$: C, 61.29; H, 6.12; N, 17.02. Found: C, 61.60; H, 6.14; N, 17.30.

Example 67

Preparation of 3-(3-hydroxypropyl)benzo[b]thiene-5-carboxamide

To an acetonitrile solution (180 mL) was added 50% HF(aq) (10 mL) and 3-[3-[(dimethyl-1,1-dimethylethylsilyl)oxy]propyl]benzo[b]thiene-5-carboxamide (4.18, 12.0 mmol). After stirring at 22° C. for one hour, K₂CO₃ (~20 g) was added portion wise. Upon cessation of effervescence the reaction was filtered and concentrated in vacuo. The concentrate was dissolved in THF (~250 mL) and washed with sat. NaCl. After removing the THF layer, the aqueous phase was extracted with additional THF (2×75 mL). The combined organic phases were dried with MgSO₄, filtered, and concentrated in vacuo to the title compound (2.75 g, 98%) as an amber solid.

Example 68

Preparation of 3-[3-[(dimethyl-1,1-dimethylethylsilyl)oxy]propyl]benzo[b]thiene-5-carboxamide To a THF (~125 mL) solution containing 3-[3-[(dimethyl-1,1-dimethylethylsilyl)oxy]propyl]-5-bromobenzo[b]thiene (9.36 g, 24.3 mmol) at -78° C. under Ar atmosphere was added t-BuLi (3.26 g, 51.0 mmol in hexane). Five min after the addition was complete, trimethylsilyl isocyanate (4.34 g, 37.7 mmol) was added and the reaction allowed to warm to 22° C. Saturated NaCl (~100 mL) was added and the reaction was transferred to a separatory funnel. The organic was isolated and the aqueous phase re-extracted with Et₂O (50 mL). The combined organic extracts were dried with MgSO₄, filtered, and concentrated in vacuo. Silica gel chromatography (95:5 CH₂Cl₂:MeOH) of the concentrate afforded the title compound (4.18 g, 49%) as an amber solid.

Example 69

Preparation of 3-[3-[(dimethyl-1,1-dimethylethylsilyl)oxy]propyl]-5-bromobenzo[b]thiene To a CH₂Cl₂ solution containing 5-bromobenzo[b]thiene-3-propanol (7.46 g, 27.5 mmol), triethylamine (4.18 g, 41.3 mmol), and 4-dimethylaminopyridine (catalytic amt) was added dropwise dimethyl-1,1-dimethylethylchlorosilane (6.22 g, 41.3 mmol). After stirring for 16 h the reaction was extracted with 1N HCl (100 mL). The organic phase was dried with MgSO₄, filtered, and concentrated in vacuo. Silica gel chromatography (CH₂Cl₂) of the concentrate afforded the title compound (9.36 g, 88%) as an amber oil.

Example 70

Preparation of t-butyl 5-bromobenzo[b]thiene-3-propanoate

The title compound was prepared in a manner analogous to the preparation of t-butyl 5-fluorobenzo[b]thien-3-propanoate (Example 54).

Example 71

Preparation of 1-[3-(5-bromobenzo[b]thien-3-yl)propyl]-4-(3-methoxy-2-pyridinyl)piperazine hydrochloride The title compound was prepared (0.49 g, 91%, mp 187°–187.5° C.) in a manner analogous to the preparation of 1-[3-(5-fluorobenzo[b]thien-3-yl)propyl]-4-(5-methoxy-4-pyrimidinyl)piperazine (Example 52) by the reaction of 5-bromo-3-benzo[b]thienpropanol tosylate with 1-(3-methoxy-2-pyridinyl)piperazine.

Anal. calcd. for C₂₁H₂₄BrN₃OS/1.0HCl: C, 52.24; H, 5.22; N, 8.70. Found: C, 51.95; H, 4.91; N, 8.40. DCI MS: (M+H)⁺ m/e=446.

Example 72

Compounds of the invention were tested for their ability to inhibit serotonin reuptake. Determination of endogenous monoaminergic reuptake inhibition values for serotonin was accomplished using test methods described by P. Skolnick et al., Br. J. Pharmacology (1985), 86, pp. 637–644; with only minor modifications.

In vitro IC₅₀ (nM) test values were determined for representative compounds of Formula I based on their inhibition of synaptosomal reuptake of tritiated serotnin.

Reasonable variations, such as those which would occur to a skilled artisan, can be made herein without departing from the scope of the invention.

We claim:

1. A compound of Formula I or a pharmaceutically acceptable acid addition salt thereof

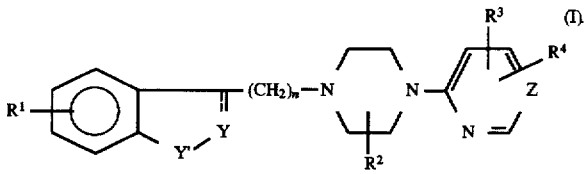

wherein

Y is CH or CH₂;

Y' is O or S;

R¹ is H, Br, Cl, F, C₁₋₄ alkyl, C₁₋₄ alkoxy, C₁₋₄ alkoxycarbonyl, CN, CONH₂ or CH₃SO₂NH;

n is 2 or 3;

R² is H or C₁₋₄ alkyl;

R³ is C₁₋₄ alkoxy;

R⁴ is H, Br, Cl, or F; and

Z is CH or N.

2. A pharmaceutical composition comprising an antidepressant amount of a compound of claim 1 and a suitable amount of a pharmaceutically acceptable carrier.

3. The compound of claim 1 wherein R¹ is H or Cl and Y' is O.

4. The compound of claim 3 wherein Y is CH₂.

5. The compound of claim 4, 1-[2-(2,3-dihydro-benzo[b]furan-3-yl)ethyl]-4-(3-methoxy-2-pyridinyl)piperazine hydrochloride.

6. The compound of claim 1 wherein R¹ is H, Cl, F, CH₃, OCH₃ or COOCH₃; Y is CH; and Y' is O.

7. The compound of claim 6 selected from the group consisting of:

1-3-(5-fluorobenzo[b]furan-3-yl)propyl]-4-(3-methoxy-2-pyridinyl)piperazine hydrochloride;

1-[3-(5-chlorobenzo[b]furan-3-yl)propyl]-4-(3-methoxy-2-pyridinyl)piperazine hydrochloride;

1-[3-(5-chlorobenzo[b]furan-3-yl)propyl]-4-(5-methoxy-4-pyrimidinyl)-2-methylpiperazine hydrochloride;

1-[3-(benzo[b]furan-3-yl)propyl]-4-(5-methoxy-4-pyrimidinyl)-3-methylpiperazine hydrochloride;

1-[3-(5-methylbenzo[b]furan-3yl)propyl]-4-(5-methoxy-4-pyrimidinyl)-2-methylpiperazine hydrochloride;

1-[3-(benzo[b]furan-3-yl)propyl]-4-(3-methoxy-2-pyridinyl)piperazine hydrochloride;

1-[3-(benzo[b]furan-3-yl)propyl]-4-(5-methoxy-4-pyrimidinyl)-2-methylpiperazine hydrochloride;

1-[2-(benzo[b]furan-3-yl)ethyl]-4-(3-methoxy-2-pyridinyl)piperazine hydrochloride;

1-[2-(5-chlorobenzo[b]furan-3-yl)ethyl]-4-(3-methoxy-2-pyridinyl) piperazine hydrochloride;

1-[3-(5-fluorobenzo[b]furan-3-yl)propyl-4-(5-methoxy-4-pyrimidinyl)piperazine hydrochloride;
1-[3-(benzo[b]furan-3-yl)propyl]-4-(5-methoxy-4-pyrimidinyl)piperazine hydrochloride;
1-[3-(5-methoxybenzo[b]furan-3-yl)propyl]-4-(5-methoxy-4-pyrimidinyl)piperazine hydochloride; and
1-[3-(5-methoxybenzo[b]furan-3-yl)propyl]-4-(3-methoxy-2-pyridinyl)piperazine hydrochloride.

8. The compound of claim 7, 1-[3-(benzo[b]furan-3-yl)propyl]-4-(5-methoxy-4-pyrimidinyl)-2-methylpiperazine hydrochloride.

9. The compound of claim 1 wherein $R^1$ is H and Y' is S.

10. The compound of claim 9 wherein Y is —$CH_2$—.

11. The compound of claim 10 selected from the group consisting of:
1-[2-(2,3-dihydrobenzo[b]thien-3-yl)ethyl]-4-(3-methoxy-2-pyridinyl)-2-methylpiperazine hydrochloride;
1-[2-(2,3-dihydrobenzo[b]thien-3-yl)propyl]-4-(3-methoxy-2-pyridinyl)-2-methylpiperazine hydrochloride;
1-[2-(2,3-dihydrobenzo[b]thien-3-yl)ethyl]-4-(3-methoxy-2-pyridinyl)piperazine hydrochloride;
1-[3-(2,3-dihydrobenzo[b]thien-3-yl)propyl]-4-(5-methoxy-4-pyrimidinyl)-2-methylpiperazine hydrochloride; and
1-[3-(2,3-dihydrobenzo[b]thien-3-yl)propyl-4-(3-methoxy-2-pyridinyl)piperazine hydrochloride.

12. The compound of claim 1 wherein $R^1$ is H, Br, CN, F, $NHSO_2CH_3$ or $CONH_2$; Y is CH; and Y' is S.

13. The compound of claim 12 selected from the group consisting of:
1-[3-(benzo[b]thien-3-yl)propyl]-4-(3-methoxy-2-pyridinyl)-2-methylpiperazine hydrochloride;
1-[3-(benzo[b]thien-3-yl)propyl]-4-(5-methoxy-4-pyrimidinyl)-3-methylpiperazine hydrochloride;
1-[3-(benzo[b]thien-3-yl)propyl]-4-(3-methoxy-2-pyridinyl)piperazine fumarate;
1-[2-(benzo[b]thien-3-yl)ethyl]-4-(3-methoxy-2-pyridinyl)piperazine hydrochloride;
1-[2-(benzo[b]thien-3-yl)ethyl]-4-(3-methoxy-2-pyridinyl)-2-methylpiperazine hydrochloride;
1-[3-benzo[b]thien-3-yl)propyl]-4-(5-methoxy-4-pyridinyl)piperazine hydrochloride;
1-[3-(benzo[b]thien-3-yl)propyl]-4-(5-chloro-3-methoxy-2-pyridinyl)-2-methylpiperazine hydrochloride;
1-[3-(5-fluorobenzo[b]thien-3-yl)propyl]-4-(5-methoxy-4-pyrimidinyl)-2-methylpiperazine hydrochloride;
1-[2-(benzo[b]thien-3-yl)ethyl]-4-(5-methoxy-4-pyrimidinyl)-3-methylpiperazine hydrochloride;
1-[3-(5-cyanobenzo[b]thien-3-yl)propyl]-4-(5-methoxy-4-pyrimidinyl)piperazine hydrochloride;
1-[3-(5-bromobenzo[b]thien-3-yl)propyl]-4-(3-methoxy-2-pyridinyl)piperazine hydrochloride;
1-[3-(benzo[b]thien-3-yl)propyl-4-(5-methoxy-4-pyrimidinyl)-2-methylpiperazine hydrochloride;
1-[3-(5-fluorobenzo[b]thien-3-yl)propyl]-4-(5-methoxy-4-pyrimidinyl)piperazine hydrochloride; and
1-[3-(5-fluorobenzo[b]thien-3-yl)propyl]-4(5-methoxy-4-pyrimidinyl)-3-methylpiperazine hydrochloride.

14. A method of treating depression in a patient comprising administering thereto an antidepressant amount of a compound of claim 1.

* * * * *